United States Patent
Duerig et al.

(10) Patent No.: US 6,312,455 B2
(45) Date of Patent: *Nov. 6, 2001

(54) STENT

(75) Inventors: Thomas Duerig, Fremont; Dieter Stöckel, Los Altos; Janet Burpee, Santa Clara, all of CA (US)

(73) Assignee: Nitinol Devices & Components, Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 42 days.

(21) Appl. No.: 08/846,130

(22) Filed: Apr. 25, 1997

(51) Int. Cl.$^7$ .................................................. A61M 29/00
(52) U.S. Cl. .................................. 623/1; 623/12; 606/198
(58) Field of Search .................................. 606/198, 191, 606/195; 623/1, 12

(56) References Cited

U.S. PATENT DOCUMENTS

| | | | |
|---|---|---|---|
| 4,390,599 | 6/1983 | Broyles | 428/597 |
| 4,631,094 | 12/1986 | Simpson et al. | 148/11.5 |
| 4,740,253 | 4/1988 | Simpson et al. | 148/11.5 |
| 4,770,725 | 9/1988 | Simpson et al. | |
| 5,147,370 | 9/1992 | McNamara et al. | |
| 5,514,154 | 5/1996 | Lau et al. | |
| 5,551,871 | 9/1996 | Besselink et al. | |
| 5,584,695 | 12/1996 | Lal Sachdeva et al. | |
| 5,607,442 | 3/1997 | Fischell et al. | |
| 5,609,627 | 3/1997 | Goicoechea et al. | |
| 5,618,299 | 4/1997 | Khosravi et al. | |
| 5,637,089 | 6/1997 | Abrams et al. | |

FOREIGN PATENT DOCUMENTS

| | | | |
|---|---|---|---|
| 484 805 | 10/1991 | (EP) | C22C/19/03 |
| 491 349 | 12/1991 | (EP) | A61M/25/01 |
| 812 928 | 6/1997 | (EP) | C22F/1/10 |

Primary Examiner—Michael H. Thaler

(57) ABSTRACT

A stent for use in a lumen in a human or animal body, has a generally tubular body formed from a shape memory alloy which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen. The shape memory alloy comprises nickel, titanium and from about 3 at. % to about 20 at. %, based on the weight of the total weight of the alloy composition, of a ternary element selected from the group consisting of niobium, hafnium, tantalum, tungsten and gold. The ratio of the stress on loading to the stress on unloading at the respective inflection points on the loading and unloading curves is at least about 2.5:1, and the difference between the stresses on loading and unloading at the inflection points at least about 250 MPa.

13 Claims, 3 Drawing Sheets

STENT

BACKGROUND OF THE INVENTION

This invention relates to a stent. Stents are used in lumens in a human or animal body. When properly positioned in a lumen, a stent can contact the wall of the lumen to support it or to force the wall outwardly.

Stents can be made from a material which enables the stent to be compressed transversely elastically so that they can then recover outwardly when the compressing force is removed, into contact with the wall of the lumen. The enhanced elastic properties available from shape memory alloys as a result of a transformation between martensite and austenite phases of the alloys make them particularly well suited to this application. The nature of the superelastic transformations of shape memory alloys is discussed in "Engineering Aspects of Shape Memory Alloys", T. W. Duerig et al, on page 370, Butterworth-Heinemann (1990). Subject matter disclosed in that document is incorporated in this specification by this reference to the document.

A principal transformation of shape memory alloys involves an initial increase in strain, approximately linearly with stress. This behaviour is reversible, and corresponds to conventional elastic deformation. Subsequent increases in strain are accompanied by little or no increase in stress, over a limited range of strain to the end of the "loading plateau". The loading plateau stress is defined by the inflection point on the stress/strain graph. Subsequent increases in strain are accompanied by increases in stress. On unloading, there is a decline in stress with reducing strain to the start of the "unloading plateau" evidenced by the existence of an inflection point along which stress changes little with reducing strain. At the end of the unloading plateau, stress reduces with reducing strain. The unloading plateau stress is also defined by the inflection point on the stress/strain graph. Any residual strain after unloading to zero stress is the permanent set of the sample. Characteristics of this deformation, the loading plateau, the unloading plateau, the elastic modulus, the plateau length and the permanent set (defined with respect to a specific total deformation) are established, and are defined in, for example, "Engineering Aspects of Shape Memory Alloys," on page 376.

SUMMARY OF THE INVENTION

The stress strain behaviour of a shape memory alloy component which exhibits enhanced elastic properties can exhibit hysteresis, where the stress that is applied at a given strain during loading is greater than the stress exerted at that strain during unloading. It is generally desirable when exploiting the enhanced elastic properties of a shape memory alloy component to minimise the difference between the stresses on the loading and unloading curves in a deformation cycle (that is to minimise the hysteresis). However, according to the present invention, it has been found that it can be advantageous in a stent to make use of an alloy which is capable of exhibiting a large hysteresis in a loading and unloading cycle. This can be obtained by using certain nickel titanium based alloys, with ternary additions of at least one of niobium, hafnium, tantalum, tungsten and gold.

Accordingly, in one aspect, the invention provides a stent for use in a lumen in a human or animal body, which has a generally tubular body formed from a shape memory alloy which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen, the shape memory alloy comprising nickel, titanium and from about 3 atomic percent (hereinafter at. %) to about 20 at. %, based on the weight of the total weight of the alloy composition, of at least one additional element selected from the group consisting of niobium, hafnium, tantalum, tungsten and gold.

The use of the specified ternary elements in a nickel titanium alloy has the advantage that the resulting stent is able to exhibit a wider hysteresis in the stress-strain behaviour in a loading and unloading cycle. This is particularly advantageous in a stent for use in a lumen in a human or animal body, which is moved through the stent while in a transversely compressed configuration from which it can expand elastically into contact with and to support the lumen. The wide hysteresis means that the inward force required to compress the stent transversely once in place in the lumen is relatively high, while the outward force that the stent exerts on the lumen as it attempts to revert to its original undeformed configuration is relatively low. This can also mean that the lumen will be resistant to being crushed by externally applied forces which can be a problem in the case of lumens close to the surface such as arteries in the thigh and neck. It can also mean that the lumen does not tend to be distorted undesirably by a large outward force exerted by the stent on the lumen.

The use of the alloy specified above can enable the ratio of the stress on loading to the stress on unloading at the respective inflection points on the stress-strain curve to be at least about 2.5:1, preferably at least about 3:1, more preferably at least about 3.5:1, for example at least about 4:1, measured at body temperature. This relationship between the loading and unloading stresses in the loading-unloading cycle provides the combination of resistance to crushing of a stent-supported lumen and low outward force tending to deform the lumen, discussed above.

Accordingly, in another aspect, the invention provides a stent for use in a lumen in a human or animal body, which has a generally tubular body formed from a shape memory alloy which has been treated so that it exhibits enhanced elastic properties with a point of inflection in the stress-strain curve on unloading, enabling the body to be deformed inwardly to a transversely compressed configuration for insertion into the lumen and then revert towards its initial configuration, into contact with and to support the lumen, the ratio of the stress on loading to the stress on unloading at the respective inflection points on the stress-strain curve being at least about 2.5:1, preferably at least about 3:1, measured at body temperature.

The use of the alloy specified above can enable the difference between the stress on loading and the stress on unloading at the respective inflection points on the stress-strain curve, after deformation to a strain of 10%, to be at least about 250 MPa, preferably at least about 300 MPa, more preferably at least about 350 MPa, for example at least about 400 MPa. This relationship between the loading and unloading stresses in the loading-unloading cycle can also provide the combination of resistance to crushing of a stent-supported lumen and low outward force tending to deform the lumen, discussed above.

Accordingly, in a further aspect, the invention provides a stent for use in a lumen in a human or animal body, which has a generally tubular body formed from a shape memory alloy which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen, the difference between the stress on loading and the stress on unloading at the respective inflection points on the stress-strain curve, after deformation to a strain of 10%, being at least about 250 MPa, preferably at least about 300 MPa, more preferably at least about 350 MPa, for example at least about 400 MPa.

A further significant advantage of the use of at least some of the alloys referred to above in the stent of the invention is that their radio-opacity is enhanced compared with that of nickel-titanium shape memory alloys conventionally used for stents, greatly facilitating their use in non-invasive surgery.

The alloy used in the stent of the invention will preferably comprise at least about 3 at. %, more preferably at least about 5 at. % of one or more additional elements. The alloy will preferably comprise not more than about 15 at. %, more preferably not more than about 10 at. % of the additional element(s). The alloy will often contain just nickel and titanium in addition to elements selected from the group referred to above (as well of course of incidental amounts of other materials including impurities), although useful alloys may include two or more elements (of which at least one, and possibly all, may be selected from the group referred to above) in addition to nickel and titanium. An example of a suitable alloy for use in the stent of the invention is $Ni_{44}Ti_{47}Nb_9$. The relative amounts of the nickel and titanium components in the alloy will be selected to provide appropriate elastic properties and to ensure that the temperatures of the transitions between the martensite and austenite phases of the alloy can be arranged to be appropriate for the intended use of the stent.

Some NiTiNb alloys which can be used in the present invention are disclosed in U.S. Pat. No. 4,770,725. That document relates to NiTiNb alloys which have been found to be capable of treatment to provide a wide thermal hysteresis. Subject matter disclosed in that document is incorporated in this specification by this reference. This property is important in applications for shape memory alloys which make use of a thermally induced change in configuration. Such a change can result by first deforming an article made from the alloy is from a heat-stable configuration to a heat-unstable configuration while the alloy is in its martensite phase. Subsequent exposure to increased temperature results in a change in configuration from the heat-unstable configuration towards the original heat-stable configuration as the alloy reverts from its martensite phase to its austenite phase.

The wide thermal hysteresis that is available by thermal and mechanical treatment of the alloys disclosed in U.S. Pat. No. 4,770,725 is attractive for articles which make use of a thermally induced configuration change since it enables an article to be stored in the deformed configuration in the martensite phase at the same temperature at which it will then be in use, in the austenite phase. While the wide hysteresis that is referred to in U.S. Pat. No. 4,770,725 confers certain advantages when the thermally induced changes in configuration are to be exploited, a wide hysteresis in stress-strain behaviour on loading and unloading is generally inconsistent with the properties of an alloy that are looked for when its enhanced elastic properties are to be exploited.

The alloy used in the stent will be treated so as to provide appropriate elastic properties for the intended application. The treatment will generally involve a combination of thermal and mechanical treatment steps. Non-linear superelastic properties can be introduced in a shape memory alloy by a process which involves cold working the alloy for example by a process that involves pressing, swaging or drawing. The cold working step is followed by an annealing step while the component is restrained in the configuration, resulting from the cold working step at a temperature that is sufficiently high to cause dislocations introduced by the cold working to combine and dislocations to align. This can ensure that the deformation introduced by the cold work is retained.

The technique for introducing superelastic properties can be varied from that described above. For example, instead of subjecting the alloy to a heat treatment while restrained in the deformed configuration, the alloy could be deformed beyond a particular desired configuration and then heat treated such that there is a thermally induced change in configuration of the kind discussed below, the change taking the configuration towards the particular desired configuration. Introduction of the superelastic properties might also involve annealing at high temperature (for example towards the recrystallisation temperature of the alloy), followed by rapid cooling and then a heat treatment at a lower temperature.

An example of a treatment that can be applied to a $Ni_{44}Ti_{47}Nb_9$ alloy to provide suitable enhanced elastic properties includes cold working the article by at least about 20%, preferably at least about 30%. The cold work will generally be less than about 60%, preferably less than about 50%. Cold work of about 40% can be appropriate for many articles. The treatment generally includes an annealing step involving exposure to elevated temperature for a period of at least about 1 minute, preferably at least about 10 minutes, generally less than about 500 minutes, preferably less than about 60 minutes. The annealing temperature will preferably be at least about 300° C. more preferably at least about 550° C. preferably less than about 550° C. more preferably less than about 450° C.

Preferably, the $A_f$ temperature (the temperature at which the transformation from martensite phase to the austenite phase is complete) of the alloy is at least about 10° C. more preferably at least about 15° C. especially at least about 20° C. Preferably, the $A_f$ temperature of the alloy is not more than about 50° C. more preferably not more than about 40° C, especially not more than about 35° C. The $A_f$ temperature of the alloy will generally be arranged to be no more than about the body temperature that will be encountered by the stent when it is in use. A stent made from an alloy whose transformation temperatures fall within one or more of these ranges has been found to exhibit appropriate elastic properties.

The stent of the invention will generally have an apertured or open configuration which facilitates the controlled transverse compression and then outward recovery in use into contact with the wall of a lumen. The apertured configuration can comprise slits, or bigger openings. A stent with an apertured configuration can be formed by cutting a tube. It might also be formed from wire using an appropriate bonding technique (such as welding) at points where wires cross.

The configuration of the apertures in the stent will be selected to provide appropriate deformation characteristics, on both transverse compression prior to use and subsequently when the stent is disposed in a lumen. The configuration should also provide appropriate flexibility for the stent, prior to and during use. It is particularly desired that (a) the flexibility of the stent when bent relative to its longitudinal axis should be high, (b) the stent should be able to recover elastically from transverse compression, for example changing its configuration from elliptical to say circular, and (c) the radial stiffness of the stent should be high.

The stent can be made by a process which involves removing material from a sheath-like object, leaving a pattern of material with appropriate hoop portions and struts. The nature of the removal process will depend on the material of the sheath-like object. For example, the removal process may involve one or more of cutting, melting and vaporising the material. When the stent is formed from a metal material, the removal process can involve use of a laser cutting tool. Other techniques which might be used for forming the pattern in the material include stamping, cutting, and etching (especially photoetching).

The sheath-like object from which the stent is formed can be a tubular object, especially a cylindrical tube with a circular cross-section. However, the sheath can be filled with a core material. The core can support the sheath during the removal process. This can prevent or at least restrict deformation of the sheath during the removal process, and damage to the opposite side of the sheath from the point at which it is being cut by an external cutting tool. The core can be provided as a rod which can be slid into the sheath. The core and the sheath might be formed as a single article, for example by a cold drawing technique.

While the removal process referred to above is preferred for forming the stent of the invention, it might be formed in other ways, for example from wire by welding. The stent could also be made from sheet material which can be formed into a tube, for example by folding and welding.

Preferably, the wall thickness of the material of the stent less than about 1.5 mm, more preferably less than about 0.8 mm. Preferably, the wall thickness is at least about 0.1 mm, more preferably at least about 0.2 mm.

Preferably, the maximum transverse dimension (which will be its diameter when the stent has a circular cross-section) of the stent (which will be its diameter when the stent has a circular cross-section) is not more than about 40 mm, more preferably not more than about 20 mm, especially not more than about 10 mm. Preferably, its minimum transverse dimension is at least about 0.5 mm, more preferably at least about 1 mm.

The stent of the invention will be located in a lumen while in a deformed configuration in which it has been compressed transversely elastically. It will be held in this configuration by means of a restraint. The restraint can conveniently be a catheter. The stent can be discharged from the catheter in the desired location in a lumen by means of an appropriate pusher such as a wire inserted into and pushed along the catheter.

SUMMARY TO THE DRAWINGS

Figure 1:
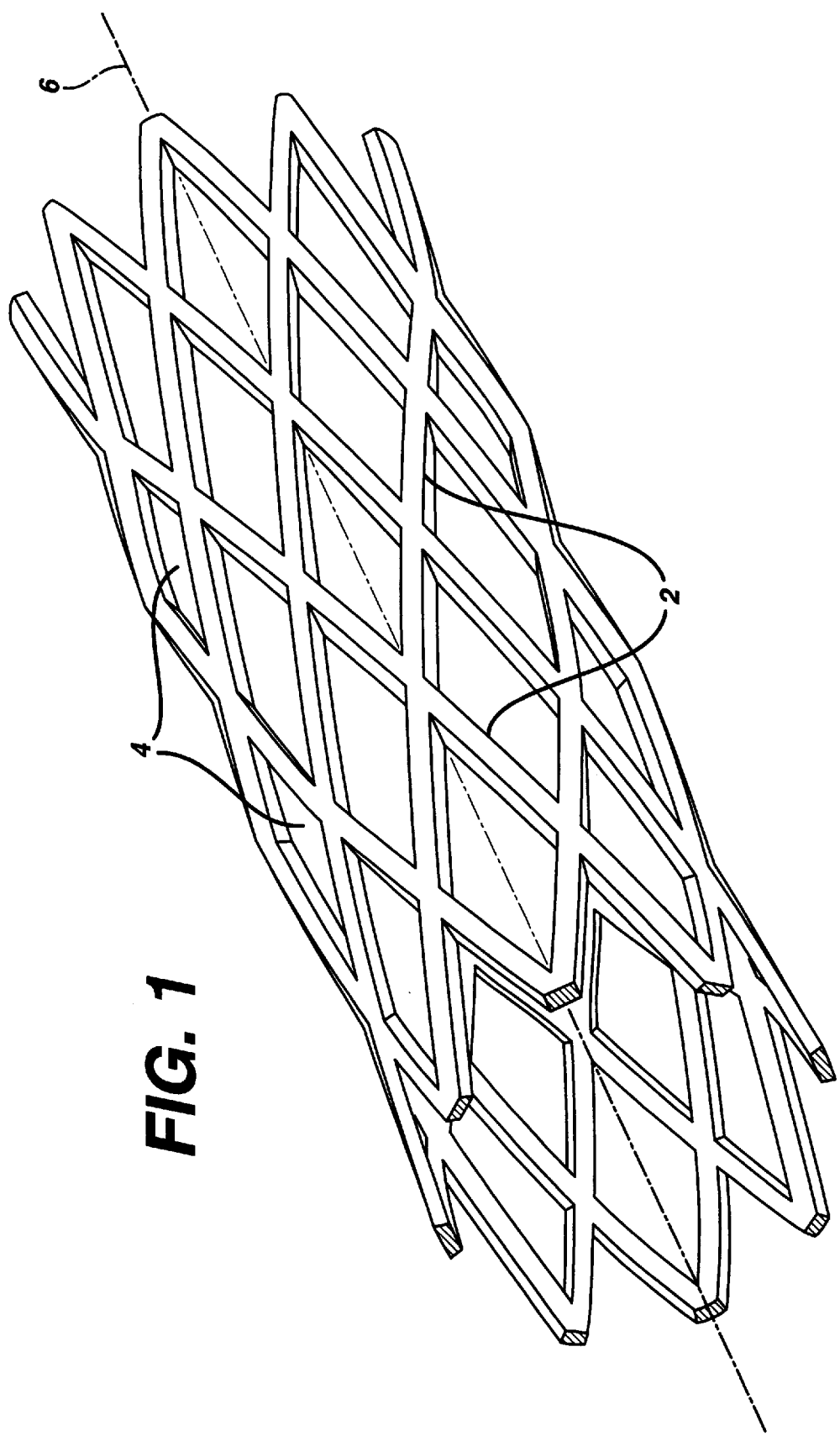
FIG. 1 is a transverse view of a stent in the configuration prior to deformation for location in a catheter in which it can be delivered to a desired position in a lumen.
Figure 2:
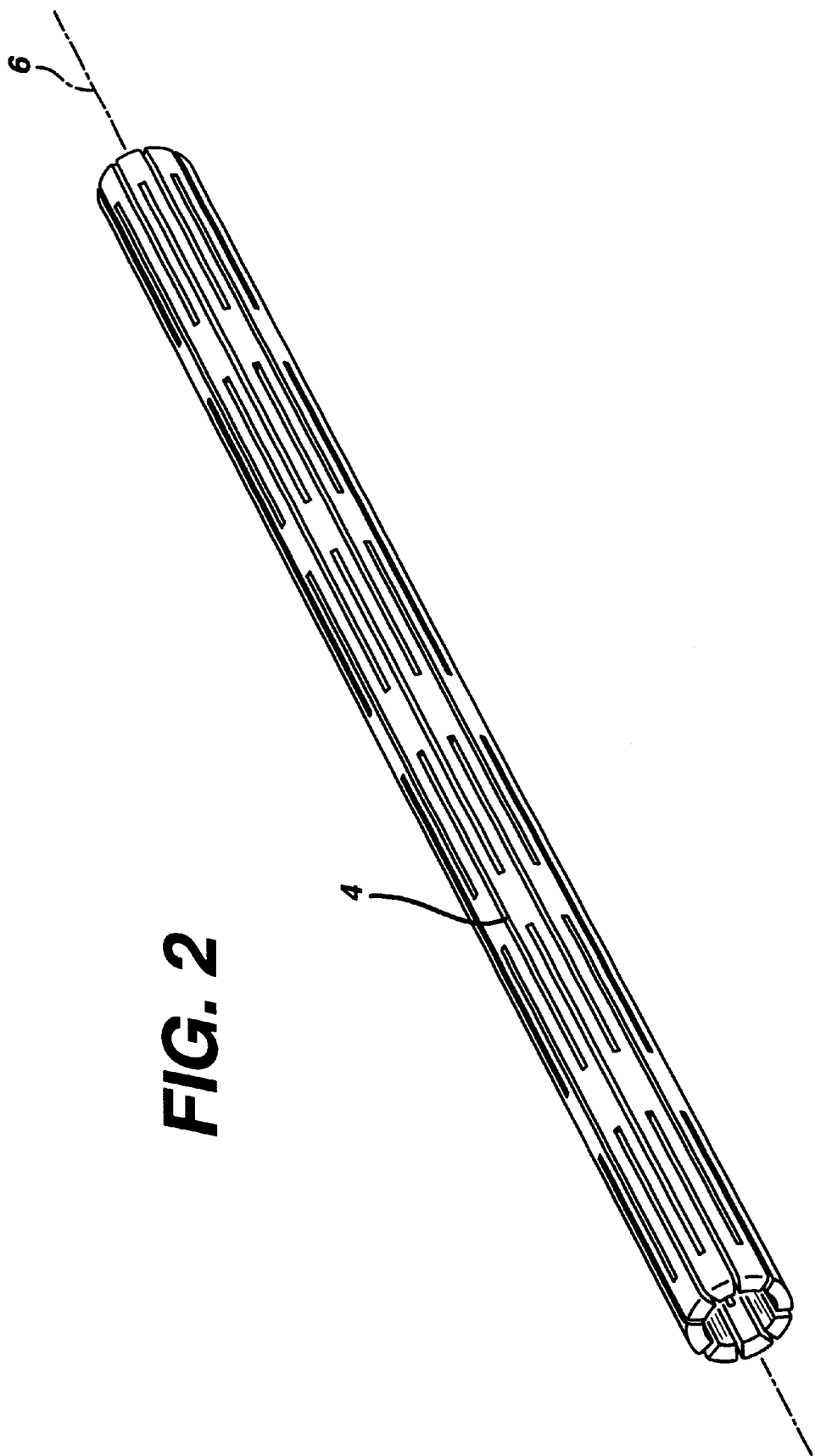
FIG. 2 is a transverse view of the stent shown in FIG. 1, after transverse deformation to a configuration in which it can be delivered to a desired position in a lumen.
Figure 3:
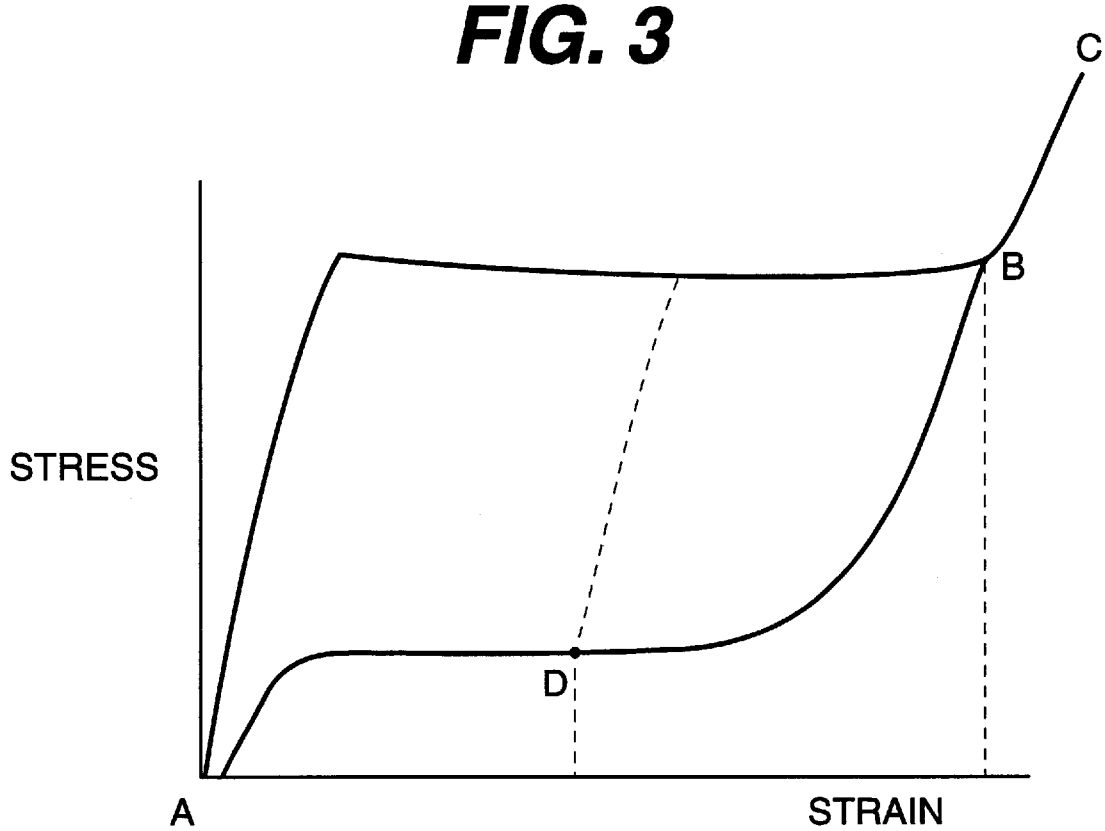

FIG. 3 demonstrates the stress-strain behaviour of the stent shown in FIGS. 1 and 2 during a loading and unloading cycle.

DESCRIPTION OF PREFERRED EMBODIMENTS

FIG. 1 shows a stent formed from an alloy which consists essentially of 44 at. % Ni, 47 at. % Ti and 9 at. % Nb. It is formed from a tube of the alloy by selective removal of the material of the alloy, for example by means of a YAG laser cutter, leaving an open array of wire-like elements 2 which define an array of diamond shaped openings 4 arranged along the longitudinal axis 6 of the tube. The openings are such that the transverse dimension of the tube (which will be its diameter if it has a circular cross-section) can be increased or decreased by changing the shape of the openings. The shape is changed by changing the angles between the wire-like elements, effectively by flattening or opening the diamond shapes of the openings.

The cut tube is treated to give the alloy enhanced elastic properties by a process involving the steps described above, including for example cold work by about 35% and annealing at about 400° C. for about 10 minutes. As a result, the stent might be capable of being deformed elastically to a strain of upto about 8.5%, and its $A_f$ temperature is about 30° C.

FIG. 2 shows the stent shown in FIG. 1 after compression so that its diameter is reduced. The reduction in diameter is accompanied by a change in the shape of the diamond shape openings 4 so that they are flattened circumferentially and elongated in a direction parallel to the axis 6 of the stent. The compression is elastic. The stent is deployed in a lumen in a human or animal body while restrained in the compressed configuration, for example by means of a catheter in which the stent is disposed for delivery. It can be compressed by means of a tapered catheter leading into the delivery catheter (in the manner of a funnel). Once appropriately located in the delivery catheter, the stent can be delivered to the desired location in the lumen. It can be discharged from the delivery catheter by means of a pusher wire, using generally known techniques.

FIG. 3 illustrates the deformation behaviour of the stent of the invention. It shows how stress varies with strain during deformation of a catheter. The behaviour is shown at a fixed temperature which, when approximately equal to the body temperature to which the stent is exposed in use, demonstrates how a stent will perform once located in a lumen. Normally, the initial deformation of the stent from the configuration shown in FIG. 1 towards that in FIG. 2 will be carried out at ambient temperature which might result in a loading curve that might differ slightly from that shown in FIG. 3.

The configuration of the stent as cut (as shown in FIG. 1) is represented by point A, where there is no strain. Compression of the stent (to the configuration shown in FIG. 2) is represented by the upper curve to point B, with a strain of about 6% and a stress of about 800 MPa. The limit of the elastic recoverable deformation of the stent is at point C: upto point C, the stent can recover at least about 90% of the initially applied strain and that strain can then be recovered repeatedly. The deformation of the stent to the configuration represented by point B can involve for example insertion into a small bore catheter, for example from a diameter of 8 mm to a diameter of 3 mm. Release of the stent without any constraint allows the stent to expand towards its initial configuration at point A along the lower curve. However, in use, the recovery of the stent is restrained by the lumen into which the stent is discharged so that the stent will adopt a configuration represented by a point D on the lower curve, between the points B and A.

From point D, the force that is exerted outwardly on the lumen as it attempts to recover further towards point A is represented by the stress on the Y-axis corresponding to point D: the stress remains substantially constant at a relatively low level as the strain is reduced. However, on compression of the stent (such as under an externally applied force in the case of a lumen close to the surface), the stent follows the dotted loading curve towards the upper loading curve, ultimately towards the point B. As the strain increases, the stress increases quickly, providing resistance to the compressive force as required to provide continued support to the lumen in which the stent is disposed.

The hysteresis loop that is apparent in the stress-strain behaviour shown in FIG. 3 has a large difference in stress between the upper loading and lower unloading curves. This difference enables the stress on continued relaxation of strain to remain low and relatively constant, and the resistance to compressive forces to be maintained low, as discussed above. The difference between the stresses on the loading and unloading curves at the respective points of inflection is about 400 MPa. The ratio between the said stresses is about 3:1.

What is claimed is:

1. A stent for use in a lumen in a human or animal, which has a generally tubular body formed from a superelastic shape memory alloy having an Af temperature less than about 15° C. which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen, the shape memory alloy comprising nickel, titanium and from about 3 at. % to about 20 at. %, based on the weight of the total weight of the alloy composition, of at least one additional element selected from the group consisting of niobium, hafnium, tantalum, tungsten and gold, the ratio of the stress on loading to the stress on unloading at the respective inflection points on the stress-strain curve being at least about 2.5:1.

2. A stent as claimed in claim 1, in which the alloy comprises at least about 5 at. % of the ternary element.

3. A stent as claimed in claim 1, in which the alloy comprises not more than about 10 at. % of the ternary element.

4. A stent as claimed in claim 1, in which the $A_f$ temperature of the alloy is at least about 10° C.

5. A stent as claimed in claim 1, in which the $A_f$ temperature of the alloy is not more than about 40° C.

6. A stent as claimed in claim 1, which comprises a plurality of wire segments extending at least partially around the circumference of the stent.

7. A stent as claimed in claim 6, which includes generally longitudinally extending portions linking the circumferential wire segments.

8. A stent as claimed in claim 1, which is located within a restraint by which it is held in a configuration in which it has been transversely compressed elastically.

9. A stent for use in a lumen in a human or animal body, which has a generally tubular body formed from a superelastic shape memory alloy having an Af temperature less than about 15° C. which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen, the ratio of the stress on loading to the stress on unloading at the respective inflection points on the stress-strain curve being at least about 2.5:1.

10. A stent as claimed in claim 9, in which the value of the said ratio is at least about 3:1.

11. A stent as claimed in claim 9, in which the shape memory alloy comprises nickel, titanium and from about 3 at. % to about 20 at. %, based on the weight of the total weight of the alloy composition, of a ternary element selected from the group consisting of niobium, hafnium, tantalum, tungsten and gold.

12. A stent for use in a lumen in a human or animal body, which has a generally tubular body formed from a superelastic shape memory alloy having an Af temperature less than about 15° C. which has been treated so that it exhibits enhanced elastic properties with a point of inflection in the stress-strain curve on loading, enabling the body to be deformed inwardly to a transversely compressed configuration for insertion into the lumen and then revert towards its initial configuration, into contact with and to support the lumen, the difference bet ween the stress on loading and the stress on unloading at the respective inflection points on the stress-strain curve, after deformation to a strain of 10%, being at least about 250 MPa.

13. A stent as claimed in claim 12, in which the shape memory alloy comprises nickel, titanium and from about 3 at. % to about 20 at. %, based on the weight of the total weight of the alloy composition, of a ternary element selected from the group consisting of niobium, hafnium, tantalum, tungsten and gold.

* * * * *